United States Patent [19]

Smedley et al.

[11] Patent Number: 5,263,942
[45] Date of Patent: Nov. 23, 1993

[54] PACKAGED PHARMACEUTICAL-TYPE SAFETY SYRINGE WITH OFF-AXIS NEEDLE CANNULA

[75] Inventors: William H. Smedley, Lake Elsinore; Terry M. Haber, Lake Forest; Clark B. Foster, Laguna Niguel, all of Calif.

[73] Assignee: Habley Medical Technology Corporation, Laguna Hills, Calif.

[21] Appl. No.: 682,088

[22] Filed: Apr. 8, 1991

[51] Int. Cl.⁵ ............................................. A61M 5/32
[52] U.S. Cl. ............................ 604/195; 604/110; 604/205; 604/232; 604/240
[58] Field of Search ............ 604/110, 125, 181, 183, 604/187, 188, 192, 195, 198, 200, 201, 205, 206, 218, 232–237, 239–240, 244; 128/919, 764, 765

[56] References Cited

U.S. PATENT DOCUMENTS

| | | | |
|---|---|---|---|
| 3,753,432 | 8/1973 | Guerra | 128/764 |
| 4,834,717 | 5/1989 | Haber et al. | |
| 4,900,307 | 2/1990 | Kulli | 604/218 |
| 4,927,414 | 5/1990 | Kulli | 604/110 |
| 4,935,014 | 6/1990 | Haber | 604/240 |
| 4,944,723 | 7/1990 | Haber et al. | |
| 5,052,403 | 10/1991 | Haber et al. | |
| 5,085,640 | 2/1992 | Gibbs | 604/218 |
| 5,147,323 | 9/1992 | Haber et al. | 604/191 |

FOREIGN PATENT DOCUMENTS

0287950 10/1988 European Pat. Off. ............ 604/110

*Primary Examiner*—C. Fred Rosenbaum
*Assistant Examiner*—Ronald K. Stright, Jr.
*Attorney, Agent, or Firm*—Townsend & Townsend Khourie & Crew

[57] ABSTRACT

A syringe (70), of the type having an adapter (76) housing a pharmaceutical-filled container (72) with a plunger (82, 86) disposed within the bore of the container barrel (74), includes a needle assembly (100) housed within a needle assembly guide (98) positioned along the exterior of the barrel. The needle assembly guide provides a path along which the needle assembly moves, between an extended position, with the needle exposed, and a retracted position, with the needle encompassed by the needle guide. The adapter includes a hollow spike (88) which pierces the septum (78) of the container to create a flow path (88, 104, 44) between the interior of the container and the needle assembly when the needle assembly is in the extended position. The needle assembly can be irreversibly locked (54, 60) in the retracted position to prevent syringe reuse.

7 Claims, 6 Drawing Sheets

PACKAGED PHARMACEUTICAL-TYPE SAFETY SYRINGE WITH OFF-AXIS NEEDLE CANNULA

CROSS REFERENCE TO RELATED APPLICATION

This application is related to U.S. Pat. application Ser. No. 07/682,058, filed on the same date as this application, for SAFETY SYRINGE WITH OFF-AXIS NEEDLE CANNULA, the disclosure of which is incorporated by reference.

BACKGROUND OF THE INVENTION

Syringes are widely used for the administration of drugs or other substances to, or for the withdrawal of fluids from, a body. Syringes are also used for a variety of health industry and other purposes as well. Typically, a syringe includes a barrel and a plunger. The plunger is reciprocally disposed within the barrel, with the plunger protruding from the proximal end of the barrel throughout its range of movement. To utilize the syringe a needle will generally be attached to the distal end of the syringe barrel, the needle being coaxial with the central axis of the barrel. The syringe may be provided with the needle pre-placed in this location, with a protective cap or sheath covering the needle. Alternatively, and more commonly, a needle with an associated sheath is attached to the distal end of a syringe barrel prior to use.

Generally, the syringe barrel and needle sheath are mass produced from a low cost material, such as polypropylene, by a cost-efficient method such as injection molding. The needle is made of a suitable material, such as 304 stainless steel.

Subsequent to use the syringe needle will often be recapped and then discarded in a suitable disposal container. In some settings the needle may be clipped prior to recapping, in an effort to preclude any illicit use of the needle after its disposal; however, clipping can release toxic and infectious aerosolization mists.

For many applications a syringe with a coaxial needle will suffice. However, there are numerous situations in which this embodiment presents significant obstacles to the effective use of the syringe. The typical syringe with a coaxial needle may have limited use when administering fluids intravenously, or particularly subcutaneously. The foregoing problems are exacerbated when larger volumes of fluid, and consequently larger diameter syringe barrels are utilized.

Furthermore, very serious, even life threatening, problems may be associated with the attachment, but more particularly with the removal, of a needle from such a syringe. The problems associated with the recapping and disposal of previously-used syringe needles are also severe. In the medical industry an exceptionally high percentage of job-related needle sticks occur during the process of needle recapping. Such needle sticks may serve as a mode for the spread of infectious disease, and are accordingly of great concern. The clipping procedure may also lead to needle sticks and/or toxic or infectious aerosolization exposure; if the syringe barrel is not also clipped it may be illicitly used once a functional needle is obtained.

SUMMARY OF THE INVENTION

The present invention is directed to a safety syringe which uses a packaged pharmaceutical container containing a liquid pharmaceutical. The liquid pharmaceutical is accessed through an access region, preferably a septum, of the container. The liquid pharmaceutical is driven out of the container, typically using a plunger which moves along the length of the container. The safety syringe has two primary features: the needle is positioned along the side of the syringe, rather than coaxially with the syringe, and the needle is a retractable needle which is irreversibly locked into a safe, post-use, retracted position in a simple and effective manner.

The syringe includes an adapter to which the packaged pharmaceutical container, preferably of the type having a barrel, is mounted. A plunger is preferably disposed within the bore of the barrel. The adapter includes a needle assembly housed within a needle assembly guide, the needle assembly guide being positioned along the exterior of the barrel. The needle assembly guide provides a path along which the needle assembly moves between an extended position, with the needle exposed, and a retracted position, with the needle encompassed by the needle guide. When the syringe is to be activated, the pharmaceutical container is preferably driven forward, that is towards the distal end of the adapter, until a hollow spike pierces the septum covering the distal end of the barrel. A flow path is created between the interior of the barrel and the needle assembly when the spike has pierced the septum and the needle assembly is in the extended position. Additionally, the needle assembly can be locked in the retracted position to prevent syringe reuse.

A primary advantage of the invention is that by providing the needle offset from the axis of the barrel, certain procedures, such as administering fluids intravenously or subcutaneously, is made easier by this radial offset by reducing the angle of incidence between the needle cannula axis and the blood vessel axis or tissue layer plane. Also, radially offset positioning permits the needle to be retracted and extended without interfering with the movement of the plunger, thus making for a simple, compact, packaged pharmaceutical-type safety syringe. The ability to use conventional packaged pharmaceutical containers permits the invention to be used with a wide variety of pharmaceuticals for enhanced flexibility.

Other features and advantages of the invention will appear from the following description in which the preferred embodiments have been set forth in detail in conjunction with the accompanying drawings.

DESCRIPTION OF THE PREFERRED EMBODIMENT

Figure 1:
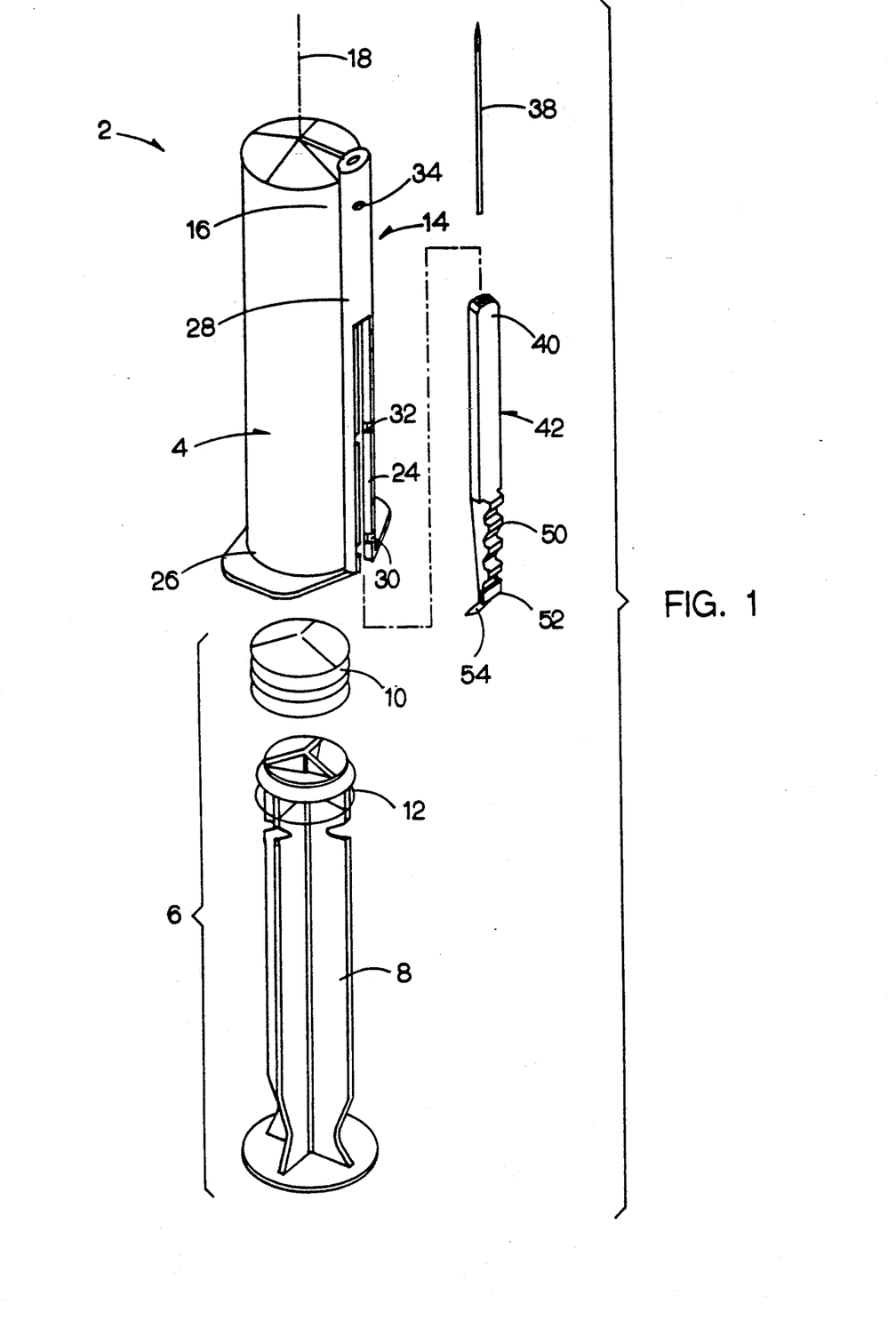
FIG. 1 is an exploded isometric view of a first embodiment of a syringe made according to the invention.

FIG. 1 illustrates a syringe 2 including a barrel 4 and a plunger 6. Plunger 6 includes a stem 8 and an elastomeric piston 10 which fits over the head 12 of stem 8. A needle assembly guide 14 is formed as a one-piece molded extension of barrel 4 positioned along the outside or exterior 16 of barrel 4. Barrel 4, guide 14 and stem 8 are preferably clear and made of a medically compatible material, such as polypropylene. Guide 14 is positioned parallel to but radially offset of the axis 18 of barrel 4. Needle assembly guide 14 is seen to be an elongate hollow member having an interior 20 which houses a needle assembly 22. Guide 14 includes a longitudinally extending slot 24 extending from the proximal end 26 of barrel 4 to a position 28 along barrel 4. Slot 24 includes a pair of cutouts 30, 32 configured to temporarily secure needle assembly 22 in the pre-use, retracted position of FIGS. 2 and 3 and the in-use, extended position of FIG. 4 as discussed below. Guide 14 also includes an access opening 34 overlying a port 36 formed in barrel 4; opening 34 permits port 36 to be molded through the wall of barrel 4.

Needle assembly 22 includes a hollow needle 38 mounted to the distal end 40 of a needle mount 42. Needle mount 42 is sized to slide within interior 20 of guide 14. As seen best in FIGS. 5 and 6, needle mount 42 includes an opening 44 which fluidly couples the interior of hollow needle 38 with port 36 when needle assembly 22 is in extended position of FIG. 4. Port 36 and opening 44 creating a flow path from a distal, variable volume region 46 defined within barrel 4 and hollow needle 38. As can be seen best in FIG. 6, the abutting surfaces 47, 48, which surround opening 44 and port 36, have complementary curved shapes to provide a good seal along the flow path formed by port 36 and opening 44.

Figure 3:
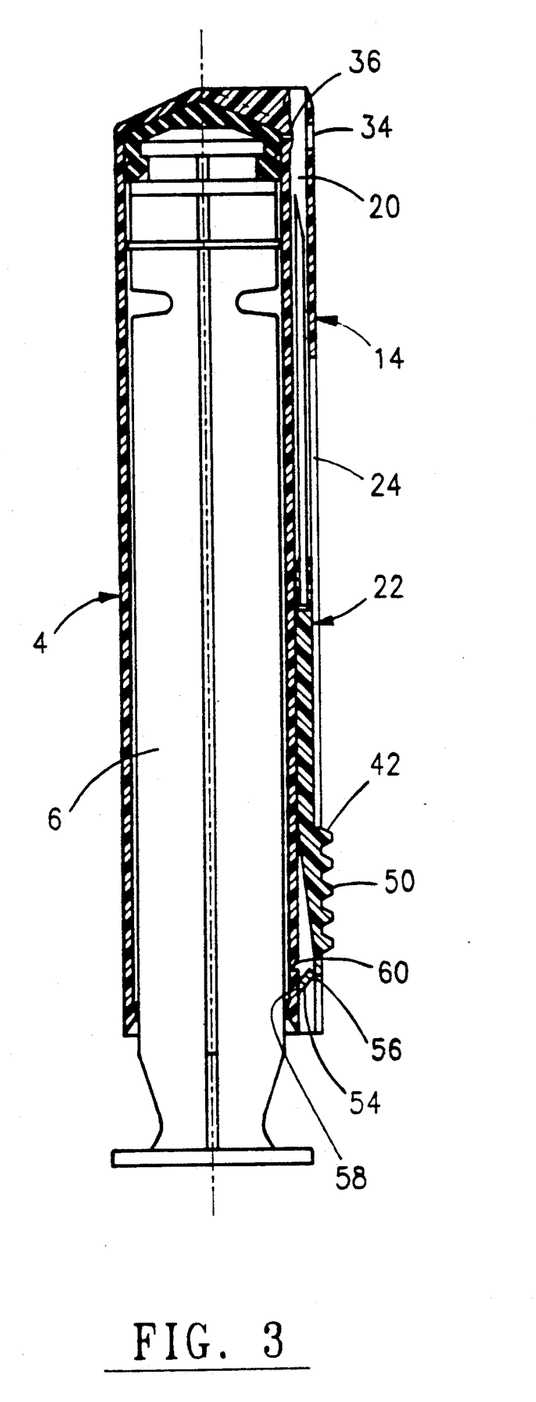
FIG. 3 is a cross-sectional view taken along line 3—3 of FIG. 2.

Needle mount 42 includes a serrated end 50 which extends through slot 24. This allows the user to move needle assembly 22 between the retracted and extended positions of FIGS. 3 and 4. To temporarily secure needle assembly 22 in the retracted and extended positions of FIGS. 3 and 4, serrated end 50 includes an extended width portion 52 sized to engage cutouts 30, 32 when needle assembly 22 is at the retracted and extended positions. As can be seen in FIGS. 3, serrated end 50 is naturally positioned in its radially outward position of FIGS. 3 and 4 so that serrated end 50 must be biased inwardly, that is towards axis 18, to disengage extended width portion 52 from cutouts 30, 32 before needle assembly 22 can be moved along interior 20 of guide 14. This keeps needle assembly 22 from inadvertently moving from its safe, pre-use, retracted position of FIG. 3 or from its in-use, extended, and potentially hazardous, position of FIG. 4.

Figure 7:
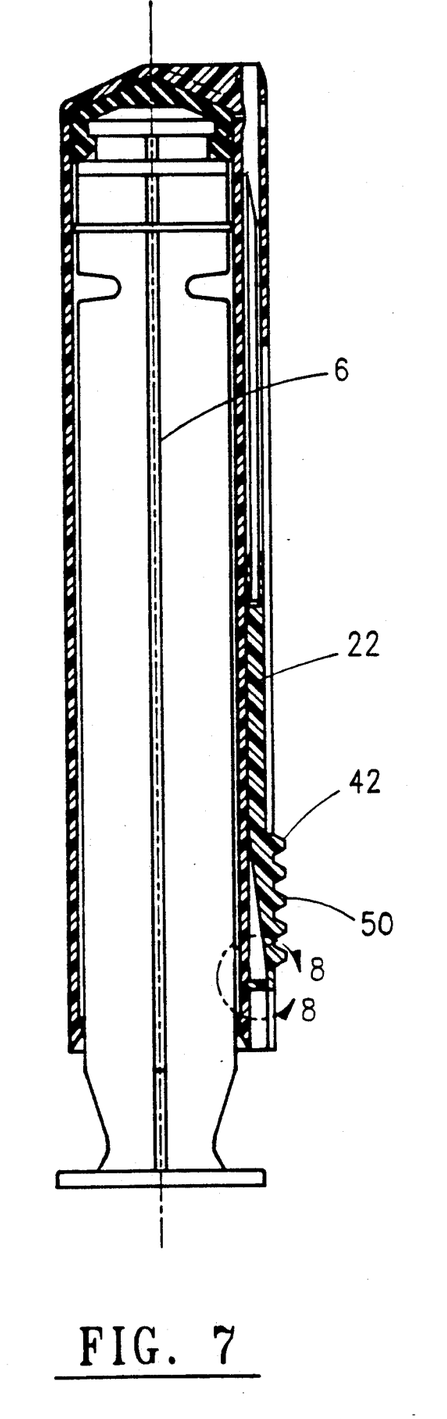
FIG. 7 illustrates the syringe of FIG. 4 after the liquid within the variable volume region has been dispensed through the hollow needle and the needle assembly has been withdrawn to its post-use, locked and retracted position.
Figure 8:
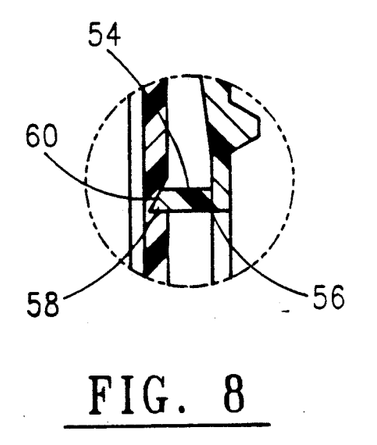
FIG. 8 is an enlarged view taken along line 8—8 of FIG. 7 shown the tab at one end of the needle mount engaging a recess stop formed in the barrel to prevent radially inward movement of the needle mount, thus locking the needle assembly in the post-use, locked and retracted position.

As can be seen in FIG. 3, needle mount 42 includes a tab 54 extending from extended width portion 52 by a hinge 56. Tab 54 has a bevelled end 58 which, due to its inclination in the pre-use, retracted position of FIG. 3, easily passes over a recess stop 60 formed in barrel 4 directly beneath cutout 30. The normal angular inclination of tab 54 in the pre-use, retracted position permits unimpeded movement of extended width portion 52 inwardly to allow portion 52 to disengage from cutout 30 in the pre-use, retracted position of FIG. 3 as well as from cutout 32 in the in-use, extended position of FIG. 4. However, the configuration and orientation of tab 54 causes the tab to engage recessed stop 60 when moved from the in-use, extended position of FIG. 4 to the post-use, retracted and irreversibly locked position of FIG. 7. This locking is illustrated best in FIG. 8. As can be seen, radially inward movement of extended width portion 52 is prevented by the engagement of tab 54 within recessed stop 60. This prevents the disengagement of extended width portion 52 from cut-out 30, thus irreversibly locking needle assembly 22 in the retracted position of FIG. 7. Syringe 2 is thus deactivated for safe, post-use disposal.

Figure 2:
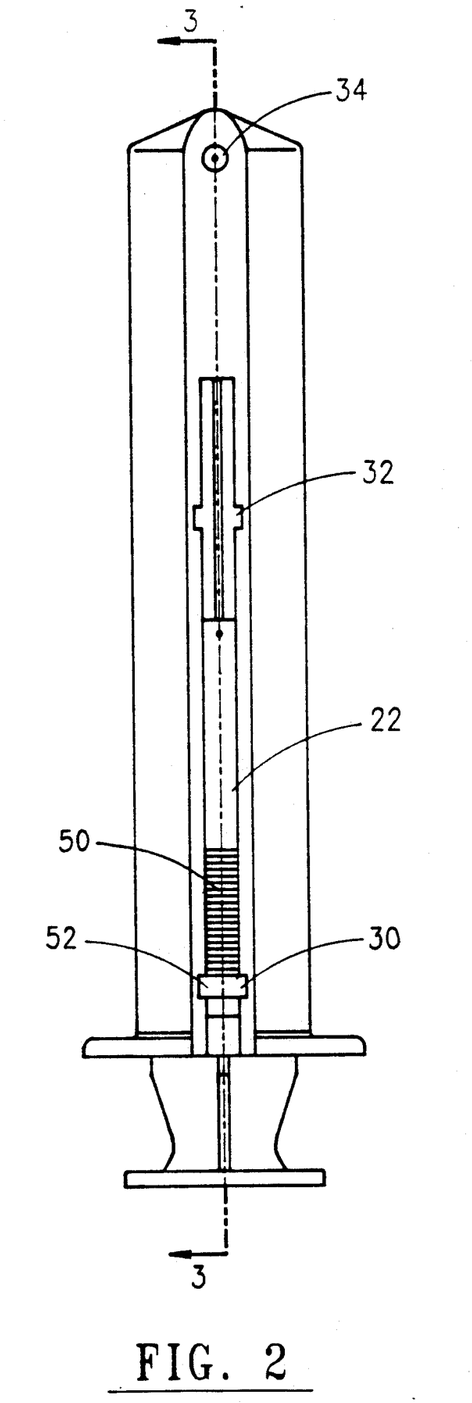
FIG. 2 is a front elevational view thereof with the plunger fully inserted into the barrel and the needle assembly in its pre-use, retracted position.
Figures 4, 5, 6:
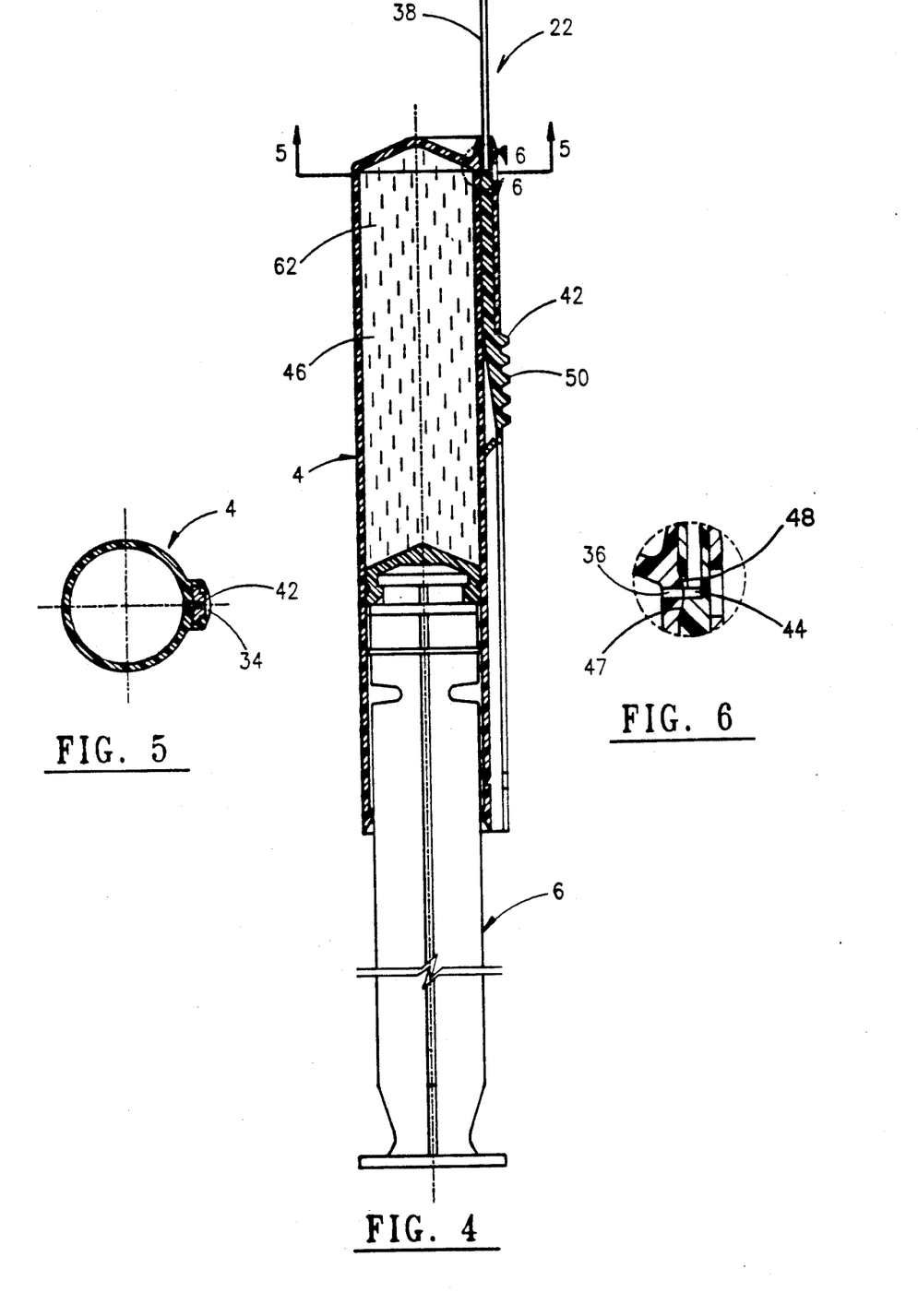
FIG. 4 shows the syringe of FIG. 3 with the needle assembly in its in-use, extended position and the plunger partially withdrawn from the barrel, thus filling the distal, variable volume region of the barrel with a liquid.
FIG. 5 is a cross-sectional view taken along line 5—5 of FIG. 4.
FIG. 6 is an enlarged view taken along line 6—6 of FIG. 4 showing the flow path fluidly coupling the variable volume region within the barrel with the hollow needle.

Syringe 2 is preferably provided in the pre-use, retracted position of FIGS. 2 and 3 in some sort of sterile packaging or wrapping. Just prior to use, syringe 2 is removed from the packaging or wrapping and needle assembly 22 is moved from the position of FIGS. 2 and 3 to the position of FIG. 4 by pressing on serrated end 50 to disengage extended width portion 52 from cutout 30. Serrated end 50 reaches the end of slot 24. Releasing serrated end 50 permits portion 52 to engage cutout 32 to temporarily lock needle assembly 20 in the extended position of FIG. 4. The tip of needle 38 is then inserted into a liquid 62 to be injected and plunger 6 is partially retracted as shown in FIG. 4 to draw liquid 62 into region 46 as illustrated in FIG. 4. The injection is then given in the normal manner, with liquid 62 passing through the flow path defined by port 36 and opening 44 and finally through needle 38. After the injection has been completed, the user presses on serrated end 50 to disengage portion 52 from cutout 32 and then draws needle assembly 22 to the post-use, retracted and irreversibly locked position of FIG. 7. In doing so, tab 54 engages recessed stop 60, thus forcing portion 52 into cutout 30 to lock needle assembly 22 in the safe, post-use, retracted and irreversibly locked position.

Figure 9:
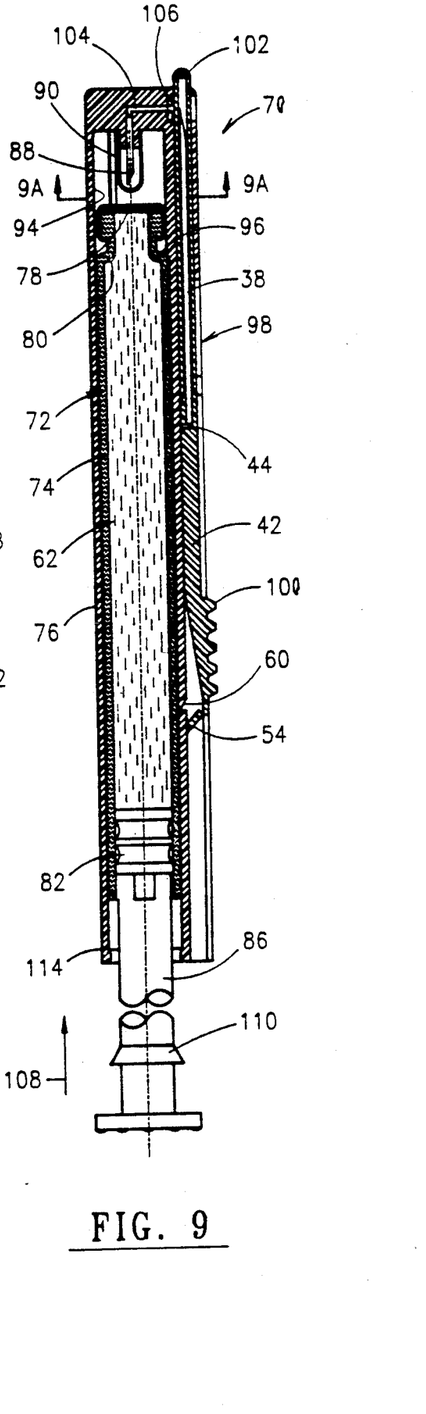
FIG. 9 is longitudinal cross-sectional view taken along line 9—9 of FIG. 11 of a further embodiment of a packaged pharmaceutical-type syringe structure made according to the invention in its pre-use, retracted position.
Figures 9A, 11:
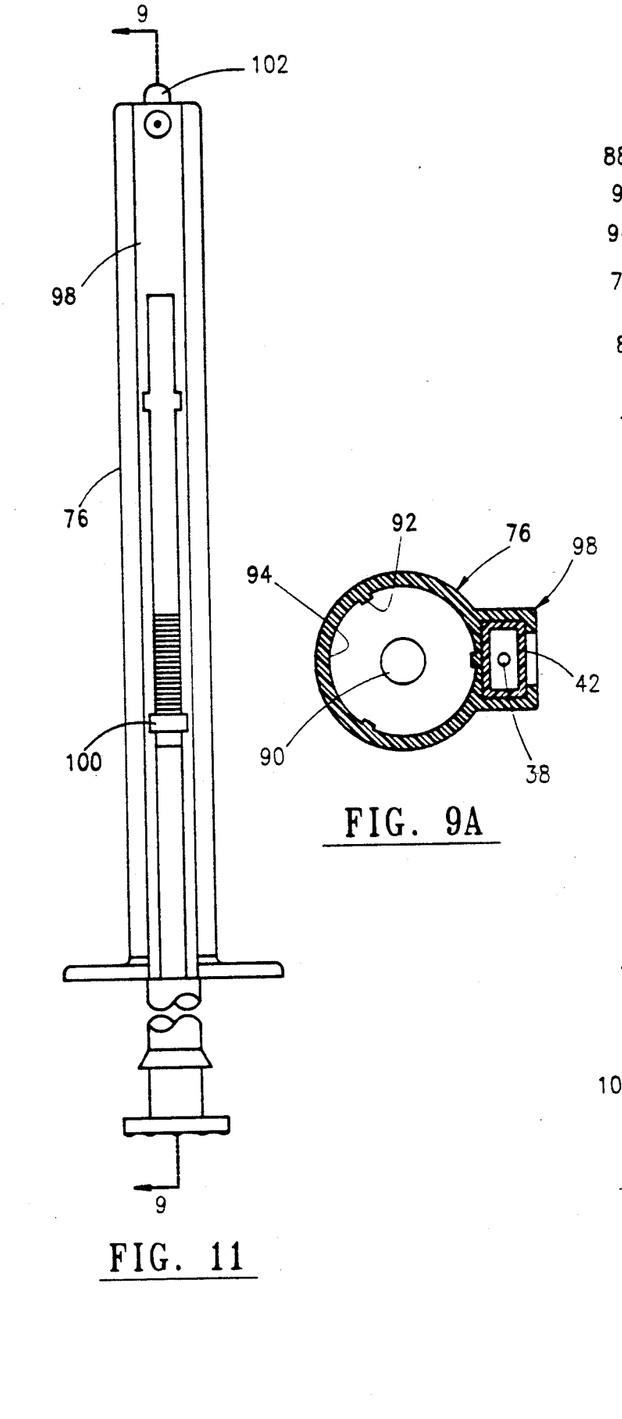
FIG. 9A is an enlarged cross-sectional view taken along line 9A—9A of FIG. 9.
FIG. 11 is an external view of the syringe structure of FIG. 9.
Figure 10:
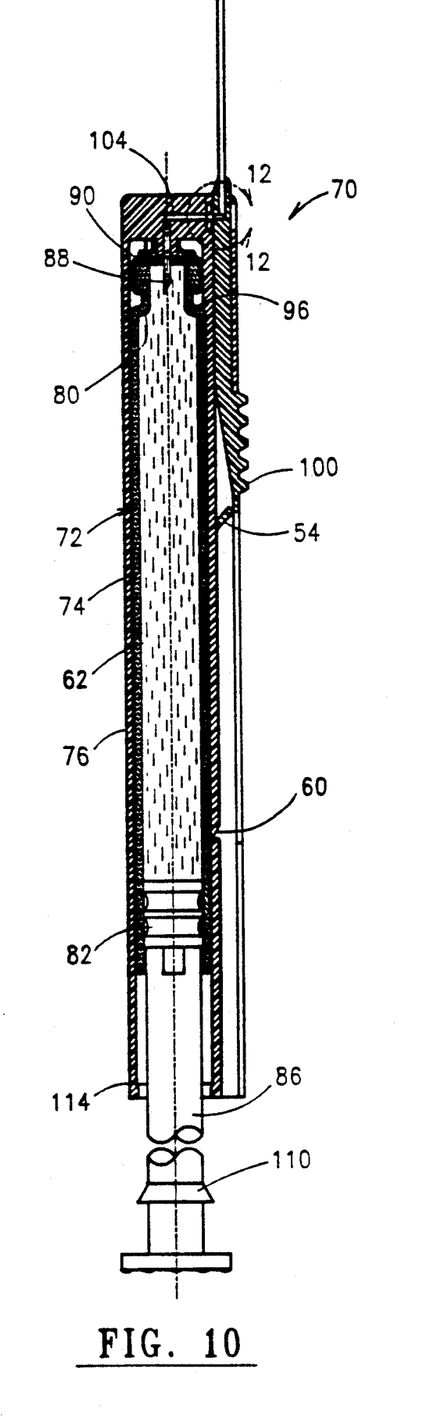
FIG. 10 shows the syringe of FIG. 9 in its activated, in-use, extended position.
Figure 12:
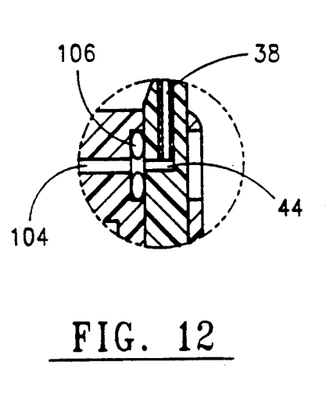
FIG. 12 is an enlarged cross-sectional view taken along line 12—12 of FIG. 10.

FIGS. 9-11 illustrate an alternative embodiment of the invention in which a syringe structure 70 is adapted for use with generally conventional packaged pharmaceutical containers 72. Container 72 includes a barrel 74 pre-filled with liquid 62 add housed within an adapter 76. Container 72 has a pierceable septum 78 at its distal end 80 and a piston 82 at its proximal end, as is conventional. A stem 86 is mounted to piston 82 during use. Adapter 76 has a spike 88 positioned opposite septum 78. Spike 88 is covered by a rupturable membrane 90 to keep the spike clean. In its pre-use, as-shipped condition of FIGS. 9 and 11, container 72 is maintained with septum 78 close to but spaced from spike 78 through the use of ribs 92 formed on the inner wall 94 of adapter 76 and extending from the distal end 95 of adapter 76 sufficient distances to engage the shoulder 96 of container 72. Syringe structure 70 may also be provided separately from container 72. Keeping syringe structure 70 in a sterile package, with or without container 72, until just before use can eliminate the need for membrane 90.

Needle assembly guide 98 is substantially the same as needle assembly guide 14 of the embodiment of FIG. 1 and thus will not be described separately. Needle assembly 100 is substantially identical to needle assembly 22 but also includes a protective sheath 102 used to cover needle 38. Adapter 76 includes a fluid path 104 which fluidly couples spike 88 to opening 44 formed in needle mount 42 when needle assembly 100 is in the extended position. To seal flow path 104 when needle assembly 100 is in both the extended and retracted positions, an O-ring 106 is used at the mouth of fluid path 104 to engage needle mount 42 and sheath 102 respectively. The operation and interengagement of needle assembly 100 with needle assembly guide 98 is substantially identical to that of syringe 2 and will thus not be separately described.

To activate syringe structure 70, stem 86 is driven in the direction of arrow 108, forcing container 72 over ribs 92, to cause membrane 90 to rupture and allow spike 88 to pierce septum 78. See FIG. 10. This preferably occurs while needle assembly 100 is in the pre-use, retracted position of FIG. 9 with flow path 104 sealed by sheath 102. When activated, needle assembly 100 is moved to its in-use, extended position of FIG. 10 to permit the injection to be given after sheath 102 is removed. Instead of moving container 72 to activate syringe structure 70, spike 88 could be modified to be movable in a manner to both pierce septum 78 and open flow path 104.

After the injection is given, a tapered ring 110 at the proximal end of stem 86 engages a ring 112 formed on inner wall 94 at a proximal end 114 of adapter 76 to prevent re-use of syringe structure 70. The user may retract needle assembly 100 from the in-use, extended position of FIG. 10 back to a post-use, retracted and locked position, similar to that shown in FIGS. 7 and 8, for disposal. The health care worker preferably does not attempt to remount sheath 102 over needle 38 prior to retracting needle assembly 100 to help reduce the chance of an inadvertent needle stick. After needle assembly 100 is retracted, sheath 102 may be placed over needle 38 to seal path 104 if desired.

Modification and variation can be made to disclosed embodiments without departing from the subject of the invention as defined in the following claims. For example, adapter 76 could be modified to be used with a conventional syringe structure having, for example, a twist-lock fitting to which a conventional needle would normally be mounted; instead of the conventional needle, adapter 76 would engage the twist-lock fitting to provide fluid access to the interior of the conventional syringe structure. Adapter 76 need not totally enclose container 72.

What is claimed is:

1. A syringe structure for use with a pharmaceutical container of the type having a barrel with a pierceable septum at a distal end, an open proximal end and a movable piston within the interior of the barrel, the syringe structure comprising;
   a stem adapted to engage the piston; an adapter including:
   an outer structure having an interior adapted to receive the pharmaceutical container;
   a needle assembly including a hollow needle and a needle mount, the needle having a central bore;
   a needle assembly guide positioned along the exterior of the outer structure, and having a needle assembly path along which the needle assembly can move between an extended position, with the needle exposed, and a retracted position, with the needle housed within the needle assembly guide;
   said needle assembly guide including first and second catches configured to engage a portion of the needle mount when the needle assembly is at the extended and retracted positions to temporarily secure the needle assembly at said positions;
   a piercing member positioned to fluidly access the interior of the barrel through the pierceable septum, the piercing member being rigidly connected to the outer structure; and
   flow path means for fluidly coupling the piercing member to the central bore of the hollow needle when the needle assembly is in the extended position so to fluidly couple the interior of the barrel with the hollow needle.

2. The syringe structure of claim 1 wherein the needle assembly guide is a one-piece extension of the cylindrical structure.

3. The syringe structure of claim 1 further comprising means for irreversibly locking the needle assembly in the retracted position.

4. A syringe structure comprising a pharmaceutical container of the type having a barrel with a pierceable septum at a distal end, an open proximal end and a movable piston within the interior of the barrel.
   an adapter mounted to the container;
   a stem mounted to the piston; and
   the adapter including:
   a needle assembly including a hollow needle and a needle mount, the needle having a central bore;
   an outer cylindrical structure housing the container;
   a needle assembly guide positioned along the exterior of the outer structure and having a needle assembly path along which the needle assembly can move between an extended position, with the needle exposed, and a retracted position, with the needle housed within the needle assembly guide;
   said needle assembly guide including first and second catches configured to engage a portion of the needle mount when the needle assembly is at the extended and retracted positions to temporarily secure the needle assembly at said positions;
   a piercing member positioned to access the interior of the barrel through the pierceable septum;
   flow path means for fluidly coupling the interior of the container at the distal end of the barrel to the central bore of the hollow needle when the needle assembly is in the extended position;
   means for irreversibly locking the needle assembly in the retracted position;
   a tab pivotally secured to the needle assembly; and means for engaging the tab as the needle assembly is moved in a direction from the extended position to the retracted position to irreversibly lock the needle assembly at the retracted position.

5. A syringe structure, for use with a pharmaceutical container of the type having a barrel with a pierceable septum at a distal end, an open proximal end and a movable piston within the barrel, the syringe structure comprising:

an adapter configured for mounting to a pharmaceutical container;

a stem able to be coupled to a piston of the pharmaceutical container;

the adapter including:

an outer structure having an interior adapted to receive the pharmaceutical container;

a hollow needle having a needle bore;

means for mounting the needle to the outer structure for movement along a path, parallel to but radially offset from the axis of the barrel, between an extended position, at which at least a portion of the needle is exposed, and a retracted position, at which the needle is enclosed within the mounting means;

the mounting means including means for temporarily securing the needle assembly in the extended and retracted positions;

a piercing member for fluidly accessing the interior of the pharmaceutical container through a pierceable septum of the pharmaceutical container; and means for fluidly coupling the piercing member with the needle bore when the needle is in the extended position so to fluidly couple the interior of the barrel with the hollow needle.

6. The syringe structure of claim 5 wherein the amounting means includes:

means for preventing movement of the movable member when the mounting means moves the needle to the retracted position from the extended position so to irreversibly lock the needle in the retracted position.

7. A syringe structure, for use with a pharmaceutical-filled container of the type having a barrel with a pierceable septum at a distal end, an open proximal end and a movable piston within the barrel, the syringe structure comprising:

an adapter having an interior sized to house a pharmaceutical filled container having a barrel with a pierceable septum at a distal end, and open proximal end and a movable piston within the barrel;

a stem able to be coupled to the piston, and extending from the proximal ends of the barrel and of the adapter;

a needle assembly including a hollow needle and a needle mount, the needle having a central bore and the needle mount including a deflectable portion;

a needle assembly guide integral with the exterior of the adapter, and having a needle assembly path along which the needle assembly can move between an extended position, with the needle exposed, and a retracted position, with the needle housed within the needle assembly guide;

the adapter including a piercing member positioned to pierce the septum of the pharmaceutical container;

a flow path, formed by the adapter and the needle assembly, fluidly coupling the interior of the barrel of the pharmaceutical container at the distal end of the barrel to the central bore of the hollow needle when the needle assembly is in the extended position;

the needle assembly guide including first and second catches configured to engage the deflectable portion of the needle mount when the needle assembly is at the extended and retracted positions to temporarily secure the needle assembly at said positions; and a tab extending from the deflectable portion and means for engaging the tab as the needle assembly is moved in a direction from the extended position to the retracted position to keep the deflectable portion engaged with the second catch thus irreversibly locking the needle assembly at the retracted position.

* * * * *